United States Patent [19]

Hamsher

[11] 4,061,867
[45] Dec. 6, 1977

[54] ACRYLATE ESTER DERIVATIVES

[75] Inventor: James J. Hamsher, Stonington, Conn.

[73] Assignee: Pfizer, Inc., 235 East 42nd St., New York, N.Y. 10017

[21] Appl. No.: 715,745

[22] Filed: Aug. 13, 1975

Related U.S. Application Data

[60] Division of Ser. No. 312,694, Dec. 6, 1972, Pat. No. 3,925,157, which is a continuation-in-part of Ser. No. 271,159, July 12, 1972, abandoned.

[51] Int. Cl.$^2$ .................................................. C07C 9/54
[52] U.S. Cl. ...................................... 560/219; 560/225
[58] Field of Search ........................ 260/486 R, 486 H

[56] References Cited

PUBLICATIONS

Holtschmidt; H., Chem. Abstr., vol. 52: P10141g, 1958.
Minsk; L. M. et al., Chem. Abstr, vol. 66: 11430d, 1967.
Minsk; L. M. et al., Chem. Abstr, vol. 67: 44576e.
Vollmert; B. et al., Chem Abstr, vol. 69: 59631j.

Primary Examiner—Paul J. Killos
Attorney, Agent, or Firm—Charles E. Lanchantin, Jr.

[57] ABSTRACT

Immobilized enzymes, intermediates therefor, and a process for the preparation of such substances are described. The method comprises reacting an enzyme with a polymerizable, ethylenically, unsaturated monomer containing a reactive group, and then polymerizing or copolymerizing the covalently-bonded enzyme-monomer product thus produced in the presence of a cross-linking agent and an initiator. The process affords immobilized enzymes of high stability and activity.

1 Claim, No Drawings

ACRYLATE ESTER DERIVATIVES

CROSS REFERENCE TO RELATED APPLICATIONS

This application is a division of application Ser. No. 312,694 filed Dec. 6, 1972, now U.S. Pat. No. 3,925,157 which is a continuation in part of application Ser. No. 271,159 filed July 12, 1972, now abandoned.

BACKGROUND OF THE INVENTION

1. Field of the Invention

Polymeric enzyme products, intermediates therefor, and their production.

2. Description of the Prior Art

Recent developments in the well established field of enzymes have been directed toward the development of stable, insoluble forms of enzymes which retain the activity of the natural enzyme. Several review articles have been published which summarize the preparation and applications of insolubilized enzymes: Orth et al., Angew. Chem. 11, 249–346 (1972); Mosbach, Acta Chem. Scand. 24, 2084–2092 (1970); Mosbach, Sc. Amer. 224, 26–33 (1971); Kay, Proc. Biochem. 3, 36–39 (1968); Goldstein et al., Z. Anal. Chem. 243, 375–396 (1968); Goldstein, "Methods in Enzymology," Academic Press, N.Y. (1971); Vol. 19, pp. 935 ff; Silman et al., Ann. Rev. Biochem., 35, 873–908 (1966); Katchalski et al., Advan. Enzymol. 34, 445 (1971). A rather comprehensive summary of the state of the art is presented in U.S. Pat. No. 3,650,900, issued Mar. 21, 1972, and by Melrose, Rev. Pure and Appl. Chem., 21, 83–119 (1971).

The various methods employed for the insolubilization of enzymes by attachment to or on a matrix fall into four principal methods: (a) covalent chemical linkage via functional groups of the enzyme that are not essential to enzyme activity; (b) entrapment or inclusion of the enzyme within a hydrophilic gel lattice which retains the enzyme but allows substrate and product to pass through; (c) ionic binding (physical adsorption) on hydrophilic ion exchangers, or on charcoal or glass beads; and (d) cross-linking them into large aggregates by reaction with bifunctional compounds.

Insoluble (immobilized) enzymes and their preparation are described in the following patents:

| | |
|---|---|
| U.S. 3,536,587 | U.S. 3,650,900 |
| U.S. 3,574,062 | U.S. 3,650,901 |
| U.S. 3,607,653 | British 1,224,947 |
| U.S. 3,616,229 | British 1,274,869 |
| U.S. 3,619,371 | German 1,935,711 |
| U.S. 3,645,852 | German 2,012,089 |

Ionic binding is not a reliable technique when a totally insoluble preparation is desired since partial or total desorption of enzyme may result from a change in ionic strength, pH or temperature, or addition of substrate.

The insolubilization of enzymes by inclusion techniques is not completely satisfactory since small amounts of enzymes leak out from such prepared gels.

The covalent linkage of enzymes to insoluble carriers offers a method of preparing water-insoluble derivatives which will not be solubilized when used or when the composition of the medium is changed provided that the covalent linkages formed are such as will not be broken under the conditions of biochemical use.

In general, the binding of a biologically active protein to an insoluble carrier by covalent bonds must be carried out via functional groups on the enzyme which are non-essential for its biological activity. The binding reaction should obviously be performed under conditions which do not cause denaturation.

Various physical attributes of the carrier such as solubility, mechanical stability, swelling characteristics and porosity, as well as its electric charge and hydrophilic or hydrophobic nature, play a major role in determining the maximal amount of enzyme which can be covalently bound, and the stability and biological activity of the insoluble product. Minimal solubility, high mechanical stability and adequate particle size are essential for the preparation of biologically-active, bound enzymes which can be readily and completely removed from reaction mixtures by filtration or centrifugation. Similar requirements must be met in the preparation of stable, biologically-active columns with well defined flow rates.

Reported immobilized enzymes include, for instance, hydrolytic enzymes such as trypsin, chymotrypsin, pepsin, pancreatin, papain, fungal and bacterial proteases, amino acid acylase, ribonuclease, phosphatase, pectinase, invertase and amylase. Of special interest is the immobilization of penicillin acylase and glucose oxidase, the enzymes responsible for the hydrolysis of a penicillin to 6-aminopenicillanic acid and a carboxylic acid, and for the conversion of glucose to glucono delta lactone, respectively. The 6-aminopenicillanic acid is used in the synthesis of "new penicillins." The chemical attachment of penicillin acylase to derivatives of cellulose and the kinetics of these immobilized preparations are described in Biotechnology and Bioengineering 11, 337–348 (1969). Other immobilized preparations of penicillin acylase are covered in British patent specification Nos. 1,183,257; 1,183,258; 1,183,260; and 1,193,918. The kinetic behavior and covalent linkage of glucose oxidase to porous glass is described in Biochemical Journal 124, 801 (1971). Glucose oxidase chemically attached to insoluble siliceous particles is discribed in U.S. Pat. No. 3,519,538.

The object of this invention is to provide new, stable, immobilized enzyme preparations with high enzyme incorporation and high enzyme activity. These stable preparations can be used repeatedly without significant loss of enzyme activity.

SUMMARY OF THE INVENTION

This invention relates to immobilized enzymes; that is, to insoluble enzyme preparations in which the enzyme is covalently attached to a polymer, to intermediates therefor, and to methods for the preparation of such substances.

The process of this invention comprises reacting a polymerizable, ethylenically unsaturated monomer which contains a reactive group with an enzyme to produce an enzyme-carrying monomer and, subsequently, polymerizing or copolymerizing the enzyme-carrying monomer in the presence of a cross-linking agent and an initiator.

Suitable polymerizable ethylenically unsaturated monomers are those having formula I

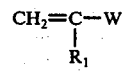

I wherein
R₁ is selected from the group consisting of hydrogen, methyl and chloro;
W, the reactive group, is selected from the group consisting of

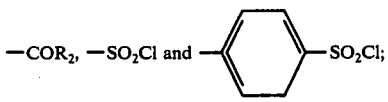

R₂ is selected from the group consisting of
(A) hydroxy,
  halide,
  azido,
  2,3-epoxypropoxy,
  2,3-epithiopropoxy,
  N-(2,3-epoxypropyl)amino,
  N-[(p-diazonium chloride)phenyl]amino,
  acryloyloxy,
  lower alkoxy carbonyloxy, and
  benzenesulfonyloxy;
and (B)    —X—(Y—X')ₙ—Z    II wherein
X and X' are selected from the group consisting of —O— and —NR₃ wherein R₃ is selected from the group consisting of hydrogen and alkyl containing from 1 to 6 carbon atoms;
Y is selected from the group consisting of alkylene containing from 2 to 3 carbon atoms;
n is an integer from 1 to 2; and
Z' is selected from the group consisting of hydrogen and Z' wherein Z' is selected from the group consisting of
  haloacetyl,
  2-(4,6-dichloro)-s-triazinyl,
  p-toluenesulfonyl,
  p(halomethyl)benzoyl, and
  cyano;
with the proviso that when Z' is p-toluenesulfonyl, X' is —O—.

Each of the monomers of formula I above wherein R₂ is a member of group (A) contains, except for those monomers wherein R₂ is hydroxy, a reactive group capable of combination with an enzyme. However, as will be recognized by those skilled in the art, when R₂ is hydroxy the monomer acids are potentially reactive in that the carboxylic group is readily activated by reaction with an appropriate carboxylic group-activating reagent, such as a carbodiimide, for example, dicyclohexyl carbodiimide or ethylmorpholinocarbodiimide; N-ethyl-5-phenylisoxazolium-3'-sulfonate (Woodward's Reagent K); ketenimines such as pentamethyleneketene, cyclohexylimine; acetylenic ethers, for example, ethoxyacetylene; hexahalocyclotriphosphatriazines; N-hydroxyphthalimide or N-hydroxysuccinimide, and other reagents used to form a peptide bond.

Monomers wherein R₂ is from group (B) are also activated with the exception of compounds in which Z is hydrogen. Such monomers, however, are transformed into reactive monomers by reaction with halo-Z' according to standard procedures and as described herein.

The monomer-enzyme product can be polymerized with an addition-polymerizable monomer in the presence of a cross-linking agent and an initiator. Suitable addition-polymerizable monomers (comonomers) are, for example, acrylic, α-chloroacrylic, methacrylic acids and the glycidyl, lower alkyl ester, N,N-(disubstituted)-aminoalkyl esters, amides, lower alkyl substituted amides, methylol substituted amides, N-monosubstituted aminoalkylamides and N,N-disubstituted aminoalkylamides thereof, styrene, butadiene and isoprene.

Polymerization or copolymerization of the monomer-enzyme product is conducted in the presence of a cross-linking agent to impart a three-dimensional network character and insolubility to the final polymer. A wide variety of cross-linking agents can be used, for example, acrylic monomers or olefin compounds and others known in the art. Representative of such agents are 1,3-butylene diacrylate, ethyleneglycol dimethacrylate, 1,3-butylene-dimethacrylate, 1,6-hexamethylene diacrylate, ethylene diacrylate, diethylene glycol dimethacrylate, N,N'-methylene-bisacrylamide, neopentyl glycol dimethacrylate, 1,1,1-trimethylol ethane trimethacrylate, divinylbenzene, and the like. The preferred cross-linking agent is N,N'-methylene-bisacrylamide since it imparts desirable hydrophilicity to the final product.

The polymerization and copolymerization reactions are initiated by free-radicals. The choice of initiator is determined largely by the mild conditions necessitated by the thermal sensitivity of the enzyme moiety. Suitable free-radical initiator systems are those which generate free-radicals at a suitable rate for polymerization or copolymerization at a temperature below about 40° C. Redox initiator systems are preferred for this reason. Representative of such systems are peroxy compounds such as ammonium, sodium, or potassium persulfate, benzoylperoxide, and peroxy carbonate in combination with a reducing agent such as sodium thiosulfate, sodium meta bisulfite, ferrous ammonium sulfate hexahydrate, dimethylaminopropionitrile or riboflavin. Dimethylaminopropionitrile is generally added to ammonium persulfate to form the preferred initiator system.

The immobilized enzymes produced by the process of this invention contain larger amounts of the active enzyme than can be achieved by covalently binding an enzyme to a finished polymer as in prior art methods. They involve no mere trapping of enzyme in the support by cross-linking between support molecules and no mere adsorption of enzyme. Electrophoresis of a sample taken after the enzyme-monomer coupling reaction shows essentially all of the enzyme is covalently bonded to the reactive monomer and, hence, to the final polymer. This accounts for the extremely high enzyme loading and enzyme activity incorporation obtainable by this process. They are of uniform character and not subject to leaching or bleeding of the enzyme from the polymer after continued use.

The binding of the enzymes to the monomers is believed to occur primarily at amino groups of the enzymes. However, enzymes generally contain a number of reactive groups which compete for reaction with and, therefore, binding to the monomer. Among such competitively reactive groups of the enzyme are sulfhydryl, hydroxyl, carboxyl and imidazolyl.

Depending upon the location of the reactive group in the enzyme, coupling with the monomer may cause a certain degree of inactivation of the enzyme. In some instances, of course, the enzyme's active or effector site may be sterically inaccessible and cause no loss in activity upon coupling of enzyme with monomer. If coupling of enzyme with monomer does give rise to undue inactivation, the active site of the enzyme may sometimes be protected in a suitable manner as by reaction with a specific reagent or competitive inhibitor, to effectively stabilize the enzyme in its active conformation and/or to expose reactive groups in the enzyme at locations apart from the active site to coupling with the monomer.

The small degree of inactivation of the enzyme which may occur on coupling with a monomer is offset in the final polymer by virtue of the fact that the process of this invention affords immobilized enzyme products having a higher active enzyme content that can be realized by the prior art methods.

A great variety of enzymes can be immobilized by the process of this invention. The review article by Melrose, Rev. Pure and Appl. Chem. 21, 83-115 (1971) lists many such enzymes. Many of the enzymes useful in the present process are readily available.

Preparations of urease, amyloglucosidase, glucose oxidase, fumarase, *Bacillus subtilis* protease and subtilopeptidase A (sometimes referred to by the trademark "Maxatase") are available from commercial sources. This latter enzyme is obtained from *Bacillus subtilis* ATCC 21839 which is the same microorganism as *Bacillus subtilis* strain R$_4$. L-Aspartase can be obtained from *Enterobacter aerogenes* ATCC 9760. Penicillin acylases can be obtained from a variety of microorganisms, U.S. Pat. Nos. 3,260,653; 3,212,995 and 3,239,427. Enzyme preparations from these microorganisms are suitable for the process of this invention, with *Proteus rettgeri* ATCC 9250, *Escherichia coli* ATCC 9637 and *Aspergillus flavus* Link ATCC 13608 the preferred microbial sources of penicillin acylase.

The immobilized enzyme preparation can be used as a slurry or in a column. At the end of the enzyme-substrate reaction, the immobilized enzyme is removed from the reaction mixture, washed with water, and set aside for subsequent repetitive use.

The following examples are given by way of illustration and are not to be construed as limitations of the invention, many variations of which are possible without departing from the spirit or scope thereof.

Preparation of Penicillin Acylase

*Proteus rettgeri* ATCC 9250 cells are grown as described in U.S. Pat. No. 3,239,427. The bacterial cells are removed from the culture broth by filtration or centrifugation, and suspended in water in the presence of 0 – 3% toluene at a level of about 5% cells by weight. The aqueous slurry is stirred for about 5 hours at 37° C., keeping the pH constant about 8.0 by careful addition of sodium hydroxide solution. The mixture is filtered or centrifuged, and the clear aqueous solution is freeze-dried or spray-dried. The material is assayed for activity as described in Biotechnology and Engineering 11, 337-348 (1969).

EXAMPLE I

Penicillin Acylase Coupling to Cyanogen Bromide Activated Hydroxyethyl Methacrylate (No Comonomer)

To a solution of 20 g. of 2-hydroxyethyl methacrylate in 80 ml. of water is added a solution of 10 g. of cyanogen bromide in 80 ml. of water. The pH is adjusted to 11.0 with 30% w/v NaOH and maintained at this pH until stabilized, keeping the temperature between 20°-30° C. The pH is brought to 6.5 with HCl, and 20 g. (8 units/mg. activity) of penicillin acylase from *Proteus rettgeri* ATCC 9250 in 200 ml. of water is added with stirring. The mixture is stirred at room temperature for 1.5 hours, then 10.0 g. of N,N'-methylene bis-acrylamide is added and the mixture stirred for an additional 30 minutes. The reaction mixture is placed in an ice bath and cooled to 4° C. under nitrogen. A catalyst system consisting of 3 ml. of dimethylaminopropionitrile and 375 mg. of ammonium persulfate is added with stirring.

The ice bath is removed and the reaction mixture is allowed to come slowly to room temperature under nitrogen. Polymerization occurs gradually over a 30–60 minute period until a thick gel results. The resulting solid is broken up, 500 ml. of water is added, and the mixture stirred to break up the thick gel into a granular solid. The solid is filtered, washed with water, and may be air-dried or vacuum-dried to give 37 g. of immobilized enzyme material which, based on activity assay, contains about 50% of the total initial activity of the free enzyme.

The immobilized penicillin acylase is capable of performing over 30 reaction runs hydrolyzing benzylpenicillin to 6-aminopenicillanic acid over a 12-week period without significant loss of activity. The conversion of benzylpenicillin to 6-aminopenicillanic acid under optimum conditions using this immobilized penicillin acylase system is greater than 95%.

EXAMPLE II

Penicillin Acylase Coupling to Cyanogen Bromide Activated Hydroxyethyl Methacrylate (Methyl Methacrylate Comonomer)

To a solution of 4.0 g. of cyanogen bromide in 65 ml. of water at 10° C. is added 10.0 g. of 2-hydroxyethyl methacrylate in 40 ml. of water. The pH is adjusted to 11.0 with 5N NaOH and maintained at this pH until constant, keeping the temperature between 10°-30° C. The pH is adjusted to 6.5 with 6N HCl and 10.0 g (5.6 units/mg. activity) of penicillin acylase from *Escherichia coli* ATCC 9637 (U.S. Pat. No. 3,260,653) in 200 ml. of water added. The mixture is stirred at 20°-30° C. for 1.5 hours, then 4.0 g. of N,N'-methylene-bis-acrylamide and 1.0 g. of methyl methacrylate are added with stirring. The mixture is cooled to 4° C. under nitrogen, then a catalyst system consisting of 1.5 ml. of dimethylamino propionitrile and 250 mg. of ammonium persulfate added with stirring. The ice bath is removed and the mixture stirred until polymerization is complete (about 1.5 hours), keeping the temperature below about 20° C. Four hundred ml. of water is added to the stirred polymer to break up the polymer into small granular particles. The mixture is filtered, and the resulting immobilized enzyme polymer stored as a wet cake. The immobilized enzyme polymer contains 45% of the total initial activity of the free enzyme. The polymer can be used for several months to deacylate penicillin G to 6-aminopenicillanic acid without significant loss in activity.

EXAMPLE III

Penicillin Acylase Coupling to Cyanogen Bromide Activated Hydroxyethyl Methacrylate (Acrylamide Comonomer)

To a solution of 15.0 g. of hydroxyethyl methacrylate in 70 ml. of water is added a solution of 7.5 g. of cyanogen bromide in 70 ml. of water. The pH is adjusted to 11.0 with 5N NaOH and maintained at this pH until constant. The temperature of the reaction mixture is maintained between 20° and 30° C.

After the reaction mixture is stabilized at pH 11.0, the mixture is adjusted to pH 6.5 with HCl and 15 g. of penicillin acylase from *Aspergillus flavus* Link ATCC 13608 in 150 ml. of water is added. The reaction mixture is stirred at room temperature for 45 minutes, then 15 g. of acrylamide and 1.5 g. of N,N'-methylene bis-acrylamide are added and the mixture stirred for 30 minutes. The mixture is placed in an ice bath and cooled to 4° C. under nitrogen and a catalyst system consisting of 3 ml. of dimethylaminopropionitrile and 350 mg. of ammonium persulfate is added with stirring. The mixture is removed from the ice bath and allowed to warm to room temperature during which time polymerization occurs, resulting in a thick gel-like solid. The solid is broken up, stirred vigorously with 1 liter of water, filtered, washed with water, and the solid freeze-dried to give 40 g. of immobilized enzyme material, with activity comparable to that of Example I.

EXAMPLE IV

Penicillin Acylase Coupling to Trichloro Triazine Activated Hydroxyethyl Methacrylate A mixture of 25 g. (0.2 mole) of hydroxyethyl methacrylate in 150 ml. of water is brought to pH 9 and 10° C. A solution of 45 g. (0.25 mole) of trichlorotriazine in 100 ml. of acetone is added to the aqueous mixture and stirred at 10°–15° C. for about 5 minutes with control of pH at 9 by monitored addition of 1N NaOH. The pH is then adjusted to 6.5 with HCl and the acetone removed in vacuo. To the resulting aqueous mixture is added a solution of 25 g. (7.0 units/mg. activity) penicillin acylase from *Proteus rettgeri* ATCC 9250 and the mixture stirred at 20° C. for 6 hours keeping the pH at 6.5–7.0 by addition of 1N NaOH. Ethylene glycol dimethacrylate (10 g.) and 2.5 g. of methyl methacrylate are added, the mixture cooled to 4° C. under nitrogen and a catalyst system of 375 mg. ammonium persulfate and 3 ml. of dimethylaminopropionitrile added with stirring. The ice bath is removed and polymerization is complete after about 2 hours resulting in a white solid. The solid is stirred with 500 ml. of water, filtered and stored as a wet cake until used. The immobilized enzyme polymer contains 35% of the total initial activity of the free enzyme and can be used repeatedly in a batch or column operation to deacylate benzylpenicillin and benzylcephalosporin to 6-aminopenicillanic acid and 7-aminocephalosporanic acid without significant loss in activity.

EXAMPLE V

Penicillin Acylase Coupling to Bromoacetyl Bromide Activated Hydroxyethyl Methacrylate To a solution of 39.04 g. (0.30 mole) hydroxyethyl methacrylate and 40 g. (0.5 mole) pyridine in 300 ml. of benzene at 6° C. is added dropwise with stirring a solution of 60.6 g. (0.30 mole) bromoacetyl bromide. After the addition is complete, the reaction mixture is stirred at 6°–8° C. for 1 hour and filtered. The filtrate is extracted with dilute HCl, the organic layer dried over magnesium sulfate, and then evaporated to dryness to give 56 g. of bromoacetoxyethyl methacrylate as a light yellow oil.

To a mixture of 17.5 g. bromoacetoxyethyl methacrylate in 50 ml. of water is added a solution of 12.5 g. (7.9 units/mg. activity) penicillin acylase from *Aspergillus flavus* Link ATCC 13608 in 150 ml. of water. The resulting mixture is brought to pH 7.75 and kept at this pH with 1N NaOH until the reaction is complete (about 5 hours). N,N'-methylene bis-acrylamide (6.25 g.) and 1.25 g. of methyl methacrylate are added and the mixture cooled to 4° C. under nitrogen. A catalyst system of 0.5 g. potassium persulfate and 2.5 ml. of dimethylamino propionitrile is added with stirring and the cooling bath removed, resulting in gradual polymerization. After polymerization is complete (about 2 hours), 200 ml. of water is added with stirring to break up the polymer into a granular solid. The mixture is filtered and the solid air-dried to give 22 g. of immobilized enzyme polymer which contains 40% of the total initial activity of the free enzyme. The immobilized enzyme polymer can be used repeatedly for several months to deacylate penicillin V to 6-aminopenicillanic acid without significant loss in activity.

EXAMPLE VI

Diimide Catalyzed Coupling of Glucose Oxidase to Hydroxyethyl Methacrylate

To a suspension of 1 g. of glucose-oxidase (activity = 4,080 IUB units /g.) and 20 mg. of hydroxyethyl methacrylate in 5 ml. of acetonitrile is added 40 mg. of 1-cyclohexyl-3-(2-morpholinoethyl)-carbodiimide metho-p-toluene sulfonate. The reaction mixture is stirred at room temperature for 17.5 hours, cooled to 4° C., placed under nitrogen, and then treated with 400 mg. of N,N'-methylene bis-acrylamide and 2.5 g. of methyl methacrylate. One gram of N,N-diethylaminoethyl methacrylate is then added dropwise, maintaining the pH at 5.8. The mixture is stirred for 10 minutes and treated with 140 mg. of ammonium persulfate and 0.5 ml. of dimethylaminopropionitrile. After warming to room temperature the reaction is stirred for 3 hours, diluted with an equal volume of water and filtered. The polymer is washed and air dried to give 5.27 g. of solids incorporating 24% of the original enzymatic activity.

EXAMPLE VII

The processes of Examples I–VI are repeated, with comparable results, replacing hydroxyethyl methacrylate with each of the monomers of the formula $$CH_2=C-\underset{R_1}{\overset{\overset{O}{\|}}{C}}-X-(Y-X')_n-H$$

| $R_1$ | X | $-(Y-X')_n-$ |
|---|---|---|
| H | O | $C_2H_4O$ |
| $CH_3$ | NH | $C_2H_4O$ |
| Cl | N—$CH_3$ | $(C_2H_4O)_3$ |
| Cl | O | $(C_2H_4O)_2$ |
| Cl | O | $(C_2H_4O)_3$ |
| $CH_3$ | O | $C_3H_6O$ |
| H | O | $(C_3H_6O)_3$ |
| $CH_3$ | NH | $C_2H_4O$ |
| $CH_3$ | $NC_6H_{13}$ | $C_2H_4O$ |
| H | NH | $C_2H_4NH$ |
| H | $NCH_3$ | $C_2H_4NCH_3$ |

Substantially the same results are obtained when the catalyst is potassium persulfate and sodium thiosulfate, sodium meta bisulfite or benzoyl peroxide and ferrous ammonium sulfate hexahydrate in place of the mixture of ammonium persulfate and dimethylaminopropionitrile.

EXAMPLE VIII

Diimide Catalyzed Coupling of Glucose Oxidase to Acrylic Acid

A solution of 5 g. of acrylic acid in 50 ml. of water is cooled to 5° C., adjusted to pH 10.5 and treated with 50 mg. of 1-cyclohexyl-3-(2-morpholinoethyl)-carbodiimide metho-p-toluene sulfonate. The reaction mixture is stirred at pH 10 for 10 minutes then adjusted to pH 6.3 with dilute hydrochloric acid. A solution of 1.5 g. of glucose-oxidase (activity = 1340 IUB units/g.) in 100 ml. of water is added and the mixture stirred at 15° C. for 19 hours. It is then cooled to 4° C., placed under nitrogen, and treated with 500 mg. of acrylamide and 2.5 g. of N,N'-methylene bis-acrylamide. The mixture is stirred for 15 minutes at 4° C. and then 1 ml. of dimethylaminopropionitrile and 280 mg. of ammonium persulfate added. After stirring at 4° C. for 15 minutes, the reaction is stirred at room temperature for 2 hours, the resultant gel diluted with water, and the pH adjusted to 4 with 2N hydrochloric acid. After stirring for 35 minutes the mixture is homogenized, centrifuged and the supernatant liquid decanted. The solid is washed again using the previous procedure and the sedimented polymer freeze-dried to give 5.5 g. of immobilized enzyme having 28% of the original total activity of the free enzyme.

EXAMPLE IX

Glucose Oxidase Coupling to Methacrylic Acid Anhydride

To a suspension of 1 g. of methacrylic acid, triethylamine salt (prepared in situ) in 5 ml. of acetonitrile is added at 5° C. 1 g. of methylacryloyl chloride. The suspension is stirred at room temperature until anhydride formation is complete and 3 g. (activity = 4,080 IUB units/g.) of glucose-oxidase is then added in one portion. After stirring for 2-5 hours the reaction mixture is placed under nitrogen, cooled to 4° C. and diluted with 16 ml. of water. N,N'-methylene bis-acrylamide (1.25 g.) and 1 g. of propyl α-chloroacrylate are added and the reaction mixture stirred for 10 minutes. While maintaining the pH at 6.5, 100 mg. of benzoyl peroxide and 100 mg. of sodium thiosulfate are added and the reaction allowed to warm to 25° C. After 2 hours, the polymer suspension is treated with an equal volume of water, filtered and washed. The immobilized enzyme system can be stored dry or as a wet cake.

EXAMPLE X

Glucose Oxidase Coupling to Methacryloyl Chloride

A suspension of 3 g. of glucose-oxidase (activity 3500 IUB units/g.), 200 mg. of methacryloyl chloride and 200 mg. of triethylamine in 5 ml. of acetonitrile is stirred for 2.5 hours at room temperature. The mixture is placed under nitrogen and cooled to 4° C. Water (8 ml.), 1.25 g. of N,N'-methylene bis-acrylamide and 1 g. of methyl methacrylate are added and the pH adjusted to 6.5 with dilute sodium hydroxide. The reaction is stirred for 10 minutes and then treated with 100 mg. of ammonium persulfate and 0.5 ml. of dimethylaminopropionitrile, maintaining the reaction pH at 6.5. After stirring at room temperature for 2 hours, the partially solidified reaction mixture is diluted with an equal volume of water, filtered and washed thoroughly with water to give 39.2 g. of wet, immobilized enzyme cake which contains 50% of the original total activity of the free enzyme. It can be used repeatedly for several months to oxidize glucose in aqueous solution to glucono delta lactone without significant loss in activity.

EXAMPLE XI

Glucose Oxidase Coupling to Methacryloyl Azide

To a suspension of 1.24 g. of sodium azide in 5 ml. of acetonitrile is added 2 g. of methacryloyl chloride. The mixture is stirred for 1 day at room temperature, and then adjusted to pH 7, cooled to 5° C. and treated with 3 g. of glucose-oxidase (activity = 4,080 IUB units/g.). It is stirred at 5° C. for 2-5 hours to maximize enzyme coupling. To the reaction mixture (under nitrogen) is added 16 ml. of water, 1.25 g. of N,N'-methylene bis-acrylamide and 1 g. of methyl methacrylate. After stirring for 10 minutes, 100 mg. of ammonium persulfate and 0.5 ml. of dimethylaminopropionitrile are added while maintaining the reaction pH at 6.5. The mixture is stirred at room temperature for 2 hours, treated with an equal volume of water, filtered and the immobilized enzyme cake washed profusely with water. The immobilized enzyme can be stored dry or as a wet cake.

EXAMPLE XII

Glucose Oxidase Coupling to Mixed Anhydride of Methacrylic Acid and Ethyl Chloroformate A suspension of 2 g. of methacrylic acid, triethylamine salt (prepared in situ) in 5 ml. of acetonitrile is treated with one equivalent of ethyl chloroformate. The reaction mixture is stirred at room temperature for 2 hours after which 3 g. of glucose-oxidase (activity = 4,080 IUB units/g.) is added and stirring continued for 5 hours. The mixture is cooled to 4° C. and 8 ml. of water, 1.25 g. of N,N'-methylene bis-acrylamide and 1 g. of N,N'-dimethyl acrylamide are added. The mixture is placed under nitrogen, adjusted to pH 6.5 and stirred for 10 minutes. One hundred milligrams of peroxy dicarbonate and a solution (ph 6) of 0.5 ml. of dimethylaminopropionitrile in 2 ml. of water are added and the reaction mixture allowed to warm to room temperature. After 2 hours it is treated with water and filtered. The filter cake is washed thoroughly and stored in the refrigerator in either wet or dry form.

EXAMPLE XIII

Glucose Oxidase Coupling to Benzenesulfonate Ester — Methacrylic Acid Mixed Anhydride To a suspension of 2.9 g. of benzenesulfonic acid, triethylamine salt (prepared in situ) in 5 ml. of acetonitrile at 0° C. is added dropwise 2 g. of methacryloyl chloride. The reaction mixture is stirred for 3 hours at room temperature and 3 g. of glucose-oxidase (activity = 4,080 IUB units/g.) added. The suspension is stirred for 5 hours, cooled and diluted with 16 ml. of water. The reaction mixture is placed under nitrogen and treated with 1.25 g. of N,N'-methylene bis-acrylamide, 1 g. of methyl methacrylate and stirred for 10 minutes. Ammonium persulfate (100 mg.) and 0.5 ml. of dimethylaminopropionitrile are then added and the pH maintained at 6.5. The reaction mixture is allowed to warm to room temperature and is then stirred for 2 hours. An equal volume of water is added to the mixture and the polymer filtered, washed and stored either at room temperature or in the refrigerator as a wet cake or dry amorphous powder.

EXAMPLE XIV

Penicillin Acylase Coupling to Diazonium Salt of N-(p-Aminophenyl)Methacrylamide To 10 g. of the diazonium salt of N-(p-aminophenyl)-methacrylamide, prepared by treating the corresponding amine with sodium nitrite, in 50 ml. of water at pH 6.5 and 10° C. is added 10 g. (6 units/mg. activity) of penicillin acylase from *Proteus rettgeri* ATCC 9250 in 200 ml. of water. The mixture is allowed to stir at 10° C. for 16 hours after which time 5 g. of neopentylglycol dimethacrylate and 1 g. of methoxyethyl methacrylate are added. The mixture is cooled to 5° C. under nitrogen and a catalyst system of 200 mg. of ammonium persulfate and 2 ml. of dimethylamino propionitrile added with stirring. The ice bath is removed and the mixture allowed to polymerize as the temperature slowly rises to 25° C. After polymerization is complete (about 2 hours), 400 ml. of water is added and the mixture stirred vigorously to break up the solid polymer into small granules. The mixture is filtered, the solid washed with water and air dried to give 18 g. of immobilized enzyme polymer which contains 42% of the total initial activity of the free enzyme. The immobilized enzyme polymer can be used repeatedly for several months to deacylate penicillin G to 6-aminopenicillanic acid without significant loss in activity.

EXAMPLE XV

Glucose Oxidase Coupling to p-Chlorosulfonyl Styrene

A suspension of 3 g. of glucose-oxidase (activity 3500 IUB units/g.), 200 mg. of p-chlorosulfonyl styrene and 200 mg. of triethylamine in 5 ml. of acetonitrile is stirred for 2.5 hours at room temperature. The mixture is placed under nitrogen and cooled to 4° C. Water (8 ml.), 1.25 g. of divinyl benzene and 1 g. of styrene are added and the pH adjusted to 6.5 with dilute sodium hydroxide. The reaction is stirred for 10 minutes and then treated with 100 mg. of ammonium persulfate and 0.5 ml. of dimethylaminopropionitrile, maintaining the reaction pH at 6.5. After stirring at room temperature for 2 hours, the partially solidified reaction mixture is diluted with an equal volume of water, filtered and washed thoroughly with water. The immobilized enzyme is stored as a wet cake at 15° C.

EXAMPLE XVI

Glucose Oxidase Coupling to Vinylsulfonyl Chloride

The method of Example XV is repeated replacing p-chlorosulfonyl styrene with vinylsulfonyl chloride.

EXAMPLE XVII

Penicillin Acylase Coupling to Glycidyl Methacrylate

To a stirred solution of 50 g. of crude penicillin acylase enzyme from *Proteus rettgeri* ATCC 9250 at 5° C. is slowly added 75 g. of glycidyl methacrylate. The resulting mixture is stirred at 15°-20° C. and pH 6-7 for 20 hours. The mixture is cooled to 5° C., purged with nitrogen for a half-hour and then 31.25 g. of N,N'-methylene bis acrylamide and 8.75 g. of methyl methacrylate are added. To this stirred mixture at 5° C. under nitrogen is added 2 g. ammonium persulfate and 10 ml. of dimethylaminopropionitrile. The stirred mixture is allowed to come to room temperature over a 2 hour period during which time polymerization is complete. The thick, granular polymer mixture is diluted with 1250 ml. of water, filtered, washed 2× with one liter of water and stored as a wet cake or suspension. The resulting polymer contains 50% of the total initial activity of the enzyme used. The immobilized penicillin acylase can be used for several months without significant loss in activity.

EXAMPLE XVIII

Penicillin Acylase Coupling to Epoxypropyl Amide and Epithio Ester of Methacrylic Acid The method of Example XVII is repeated, replacing glycidyl methacrylate (2,3-epoxypropylmethacrylate) with either 2,3-epithiopropyl methacrylate or N-(2,3-epoxypropyl)methacrylamide.

EXAMPLE XIX

The procedures described in the preceding examples are repeated but replacing penicillin acylase and glucose oxidase with urease (Worthington Biochemicals), amyloglucosidase (Amano Corp., Japan), fumarase (Worthington Biochemicals), subtilopeptidase A from *Bacillus subtillis* ATCC 21839, and L-aspartase from *Enterobacter aerogenes* ATCC 9760.

EXAMPLE XX

Use of Immobilized Urease

The enzyme urease, immobilized by the process of this invention, can be used over and over to hydrolyze urea into carbon dioxide and ammonia. The immobilized urease enzyme can be used in a continuous flow column or in a batch type process for several months without significant loss in activity.

EXAMPLE XXI

Use of Immobilized Fumarate Hydratase (Fumarase)

The enzyme fumarase, immobilized by the process of this invention, can be used to convert fumarate to L-malate at pH 7 and 25° C. in over 80% yield. The immobilized fumarase is stable for long periods of time and can be used over and over to convert fumaric acid to L-malic acid in a column or batch type process.

EXAMPLE XXII

Use of Immobilized L-Aspartate Ammonia-Lyase (L-Aspartase)

The enzyme L-aspartase, immobilized by the process of this invention, can be used to convert diammonium fumarate to L-aspartate in 90% yield at pH 7 and 25° C. The immobilized L-aspartase enzyme polymer can be used over and over again to convert fumarate to L-aspartate without significant loss in activity.

EXAMPLE XXIII

Use of Immobilized Dextrin-1,6-Glucosidase (Amyloglucosidase)

The enzyme amyloglucosidase, immobilized by the process of this invention, can be used to convert starch-hydrolyzates to glucose in 95% yield. The immobilized amyloglucosidase can be used continuously for several months to convert starch-hydrolyzates to glucose without significant loss in activity.

EXAMPLE XXIV

Use of Immobilized Subtilopeptidase A

The enzyme subtilopeptidase A, immobilized by the process of this invention, can be used continuously over a two-week period to hydrolyze casein into peptides and amino acids without significant loss in activity.

EXAMPLE XXV

Penicillin Acylase Coupled to Preformed Glycidyl Methacrylate Polymer

To a mixture of 40 g. glycidyl methacrylate in 400 ml. water is added 15 g. of N,N'-methylene bis acrylamide. After stirring for about 5 minutes the mixture is cooled to 4° C. and 4 g. of methyl methacrylate added. Nitrogen is bubbled through the stirred mixture for about 15 minutes at 4° C., after which 5 ml. of dimethylaminopropionitrile and 1 g. of ammonium persulfate are added with stirring. The mixture is allowed to come to room temperature while stirring during which time polymerization is complete. Four hundred ml. of water is added to the mixture which is stirred for 15 minutes and then filtered. The solid glycidyl methacrylate polymer is resuspended in 400 ml. of water and 70 g. of penicillin acylase from *Proteus rettgeri* ATCC 9250 (6 units/mg.) is added. The mixture is stirred for 6 hours at room temperature, filtered and washed with water to give an immobilized enzyme polymer containing 12% of the total initial penicillin acylase activity. This incorporation yield is similar to other prior art methods but is only about 30% of incorporation obtainable by the process of this invention.

What is claimed is:

1. The product produced by contacting a hydroxy-containing vinyl monomer with a cyanogen halide, said monomer having the formula

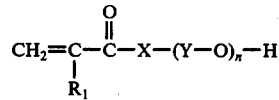

wherein
X is —O—;
Y is ethylene or propylene;
$n$ is 1 or 2; and
$R_1$ is selected from the group consisting of hydrogen, methyl and chloro.

* * * * *